US008282561B2

(12) United States Patent
Towe

(10) Patent No.: US 8,282,561 B2
(45) Date of Patent: Oct. 9, 2012

(54) PIEZO MICRO-MARKERS FOR ULTRASOUND MEDICAL DIAGNOSTICS

(75) Inventor: Bruce Towe, Mesa, AZ (US)

(73) Assignee: Arizona Board of Regents, Tempe, AZ (US)

( * ) Notice: Subject to any disclaimer, the term of this patent is extended or adjusted under 35 U.S.C. 154(b) by 1455 days.

(21) Appl. No.: 10/557,362

(22) PCT Filed: May 24, 2004

(86) PCT No.: PCT/US2004/016417
§ 371 (c)(1),
(2), (4) Date: Dec. 12, 2006

(87) PCT Pub. No.: WO2004/105583
PCT Pub. Date: Dec. 9, 2004

(65) Prior Publication Data
US 2007/0276232 A1   Nov. 29, 2007

Related U.S. Application Data

(60) Provisional application No. 60/473,242, filed on May 23, 2003.

(51) Int. Cl.
*A61B 8/14* (2006.01)
(52) U.S. Cl. ............ 600/459; 600/437; 73/587; 73/602

(58) Field of Classification Search .................. 600/437, 600/459; 73/587, 589, 596, 602
See application file for complete search history.

(56) References Cited

U.S. PATENT DOCUMENTS

| | | | |
|---|---|---|---|
| 4,706,681 A | | 11/1987 | Breyer et al. |
| 5,076,278 A | * | 12/1991 | Vilkomerson et al. ........ 600/459 |
| 6,239,724 B1 | * | 5/2001 | Doron et al. ............. 340/870.28 |
| 6,409,684 B1 | | 6/2002 | Wilk |
| 6,520,911 B1 | * | 2/2003 | Wen .............................. 600/437 |
| 6,772,490 B2 | * | 8/2004 | Toda ............................ 29/25.35 |
| 2004/0068204 A1 | * | 4/2004 | Imran et al. ................... 600/593 |

* cited by examiner

*Primary Examiner* — Brian Casler
*Assistant Examiner* — Daniel Huntley
(74) *Attorney, Agent, or Firm* — Fulbright & Jaworski L.L.P.

(57) ABSTRACT

An imaging system is disclosed that uses piezoelectric markers. The piezoelectric fields in combination with ultrasound reflections can be used to construct an image of an otherwise difficult to detect feature within a subject's body. In one embodiment, the invention includes a piezoelectric marker, including at least one piece of piezoelectric material, an ultrasound transducer connected to an ultrasound pulser and a receiver, a computer sequencing control connected to the receiver and the ultrasound pulser, a display connected to the computer sequencing control and electrodes connected to the computer sequencing control via amplification circuitry.

17 Claims, 10 Drawing Sheets

PIEZO MICRO-MARKERS FOR ULTRASOUND MEDICAL DIAGNOSTICS

BACKGROUND

The present invention relates generally to medical imaging and more specifically to the imaging of foreign objects such as medical devices that are inserted into the body of a subject.

Image contrast in conventional medical ultrasound results from differences in tissue acoustic properties. Small medical devices made from plastics or polymers are often not easily seen in ultrasound images because their acoustic properties are similar to those of the surrounding tissue. Metal objects such as biopsy needles can also be troublesome to image because they specularly reflect ultrasound. An alternative to ultrasound imaging is X-ray radiography. X-ray radiography is routinely used to position catheters or locate implanted markers, but involves radiation that can be ionizing.

SUMMARY OF TIE INVENTION

Embodiments of the present invention use piezoelectric materials to enable the imaging of foreign objects in the body of a subject using ultrasound. One aspect of the invention includes a piezoelectric marker, including at least one piece of piezoelectric material, an ultrasound transducer connected to an ultrasound pulser and a receiver, a computer sequencing control connected to the receiver and the ultrasound pulser, a display connected to the computer sequencing control and electrodes connected to the computer sequencing control via amplification circuitry.

In another embodiment, the piezoelectric marker is constructed from at least one piece of PVDF, at least one piece of PZT or PVDF-TRFE. In a further embodiment, the piezoelectric marker is constructed from multiple pieces of piezoelectric material arranged such that adjacent pieces have alternating polarities. In yet another embodiment, the piezoelectric material used in the construction of the piezoelectric marker is coated with a layer of material having an acoustic impedance that is less than the acoustic impedance of the piezoelectric marker.

In a still further embodiment, the computer sequencing control, the ultrasound pulser, the receiver and the display are implemented using a conventional ultrasound diagnostic machine.

One aspect of the method of the invention includes illuminating the object with ultrasound and forming an image using information collected from reflect ultrasound and information collected concerning electric fields. In a further embodiment of the method, the information collected concerning electric fields is delayed relative to the information collected from reflected ultrasound when forming an image. In yet another aspect of the method of the invention, the object is illuminated using pulses of ultrasound and the delay is equal to twice the time between the generation of the most recent ultrasound pulse and the time at which the electric field is observed.

DETAILED DESCRIPTION OF THE INVENTION

Turning now to the drawings, embodiments of the present invention include piezoelectric markers that generate electric fields in response to excitation by ultrasound pressure waves. The generated electric fields can be detected using electrodes to provide positional information. In several embodiments, the positional information can be combined with information from ultrasound reflections to provide an ultrasound image of a subject's body that includes the piezoelectric markers, which would otherwise be difficult to observe.

Figure 1:
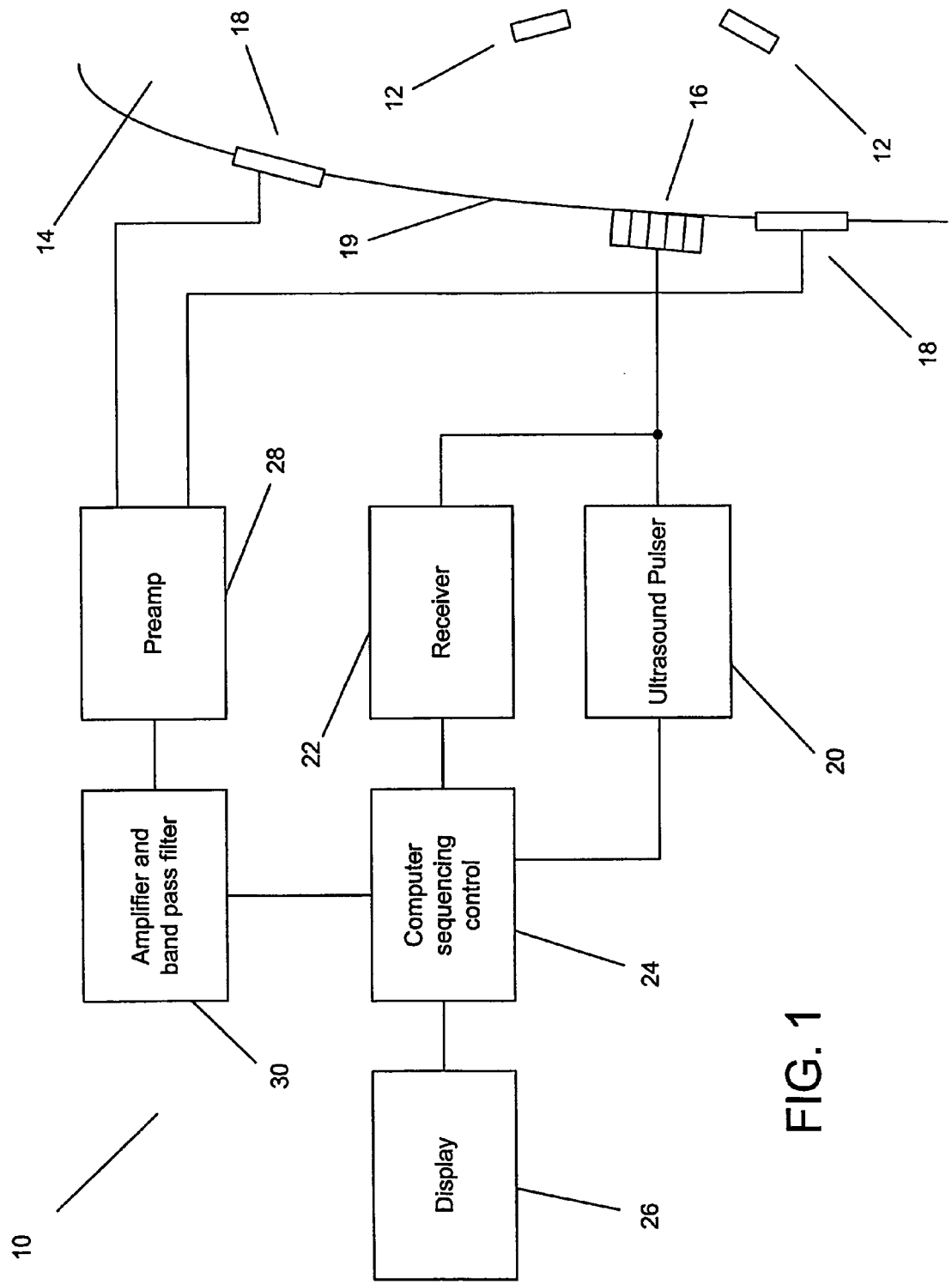
FIG. 1 is a schematic view of one embodiment of an imaging system in accordance with the present invention.

An embodiment of an imaging system in accordance with the present invention is illustrated in FIG. 1. The imaging system 10 includes at least one piezoelectric marker 12 embedded inside a subject's body 14. An ultrasound transducer array 16 is positioned external to the subject's body to direct ultrasound pressure waves into the subject's body and electrodes 18 are attached to the surface 19 of the subject's body. The ultrasound transducer array is connected to an ultrasound pulser 20 and to a receiver 22. Both the ultrasound transducer and the receiver are connected to a computer 24 that is connected to a display 26. The electrodes can be connected to a preamplifier 28, which is connected to amplification and filtration circuitry 30.

In one embodiment, the ultrasound transducer array generates pressure waves that are incident on the piezoelectric marker. The piezoelectric marker is constructed from piezoelectric materials that generate an electric field in response to excitation by the ultrasound pressure waves. The electric fields generated by the piezoelectric markers can then be detected using the electrodes. The pressure waves can be generated as brief pulses and the distance of the piezoelectric marker from the ultrasound transducer can be estimated by timing the delay between the generation of a pulse and the detection of an electric field by the electrodes.

The generation of ultrasound pulses by the ultrasound transducer array can be achieved by the computer prompting the ultrasound pulser to output a signal capable of driving the ultrasound transducer array. The generation of an ultrasound image can be achieved using the receiver and the computer to construct an image using reflected ultrasound detected using the ultrasound transducer. An image of the piezoelectric marker can then be superimposed onto the ultrasound image by interpreting signals generated by the electrodes. The computer can extract portions of the electrode signal that are indicative of the electric fields generated by the piezoelectric markers in response to excitation by pressure waves. The signals generated by the electrodes are small and can require pre-amplification prior to amplification and filtering. By timing the delay between the generation of an ultrasound pulse and the detection of a signal at the electrodes, the computer can calculate the distance of the piezoelectric marker from the ultrasound transducer. Alternatively, the computer can superimpose the signal from the electrodes over the ultrasound image by doubling the delay experienced by the electrical signals received by the electrodes to account for the difference in the speed at which electrical signals and acoustic waves propagate through the human body.

Various constructions of piezoelectric markers can be used in accordance with the present invention and the particular construction can depend upon the material that is used in the construction. A piece of piezomaterial alone may generate a sufficient electric field to be detected by electrodes on the surface of the body and hence act as a piezoelectric marker in accordance with the present invention. Alternatively, coatings may be required to increase the amount of acoustic energy converted into charge by the piezoelectric material used in the marker. In addition, electrodes on the marker may be useful in increasing the strength of the electric field generated by the piezoelectric marker. Embodiments of piezoelectric markers in accordance with the present invention are illustrated in FIGS. 2A-2F.

Figure 2A:
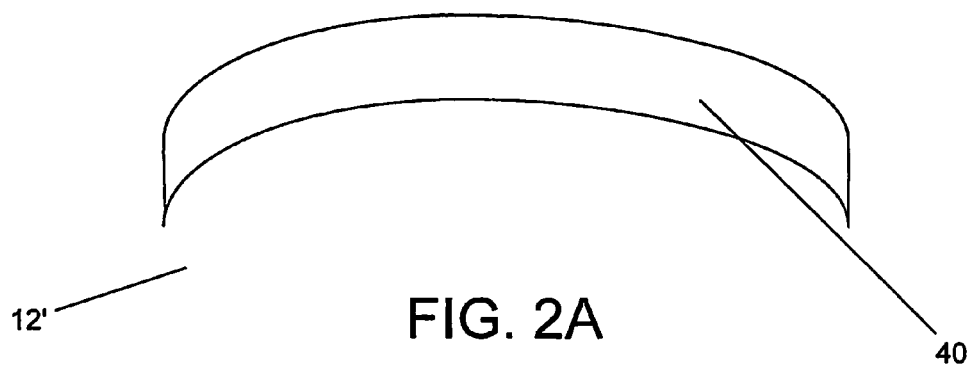
FIGS. 2A-2F are embodiments of piezoelectric markers in accordance with the present invention.

A piezoelectric marker 12' in accordance with the present invention that includes a piece of piezoelectric material 40 is illustrated in FIG. 2A. In several embodiments, the dimensions of the piezoelectric material are chosen to generate an electric field exceeding a predetermined threshold in response to excitation by a known intensity of ultrasound. Factors that can impact the generated electric field include the length, thickness and curvature (if any) of the piece of piezoelectric material. The factors that impact the choice of the dimensions of pieces of piezoelectric material that are used in the construction of piezoelectric markers are discussed in detail below.

Figure 2B:
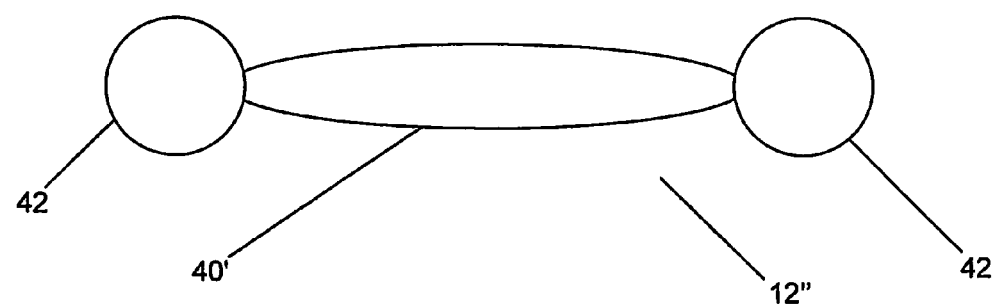

A piezoelectric marker 12" in accordance with the present invention that includes a piece of piezoelectric material 40' and two electrode contacts 42 is illustrated in FIG. 2B. In one embodiment, the piece of piezoelectric material can be rectangular. In other embodiments, the piece of piezoelectric material can be curved and in one embodiment is curved with a radius of curvature that is larger than one half wavelength of the applied ultrasound. Curved surfaces can increase the ability of a piezoelectric material to generate electric fields from ultrasound from a broader field of view of the transducer array.

Figure 2C:
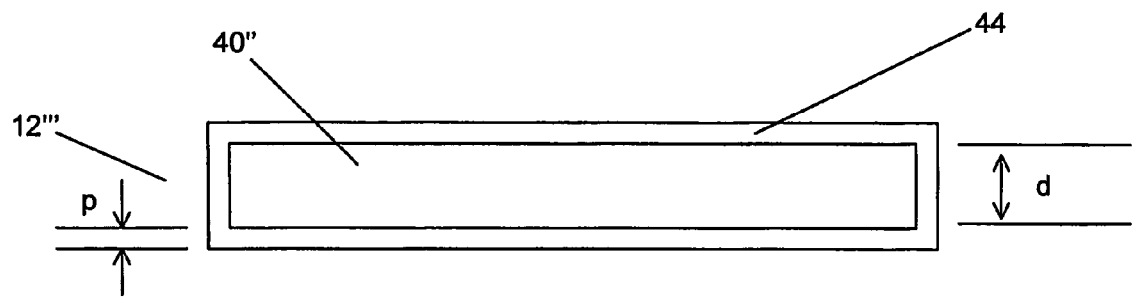

Another piezoelectric marker in accordance with the present invention is illustrated in FIG. 2C. The piezoelectric marker 12''' includes a piece of piezoelectric material 40'' that is surrounded by an electrically conductive material 44. In one embodiment, the piezoelectric material is rectangular and has a thickness d equal to half the wavelength of the ultrasound used to excite the piezoelectric marker. The layer of conducting material surrounding the piezoelectric marker has a thickness p equal to one quarter of the wavelength of the ultrasound used to excite the piezoelectric marker. These dimensions increase the ultrasound that is converted into electric charge by the piezoelectric material. The conductive layer can be constructed from any biocompatible electrically conductive material and is ideally chosen to match the acoustic impedance of the piezoelectric material with acoustic impedance of the tissue surrounding the piezoelectric marker (see discussion below).

Figure 2D:
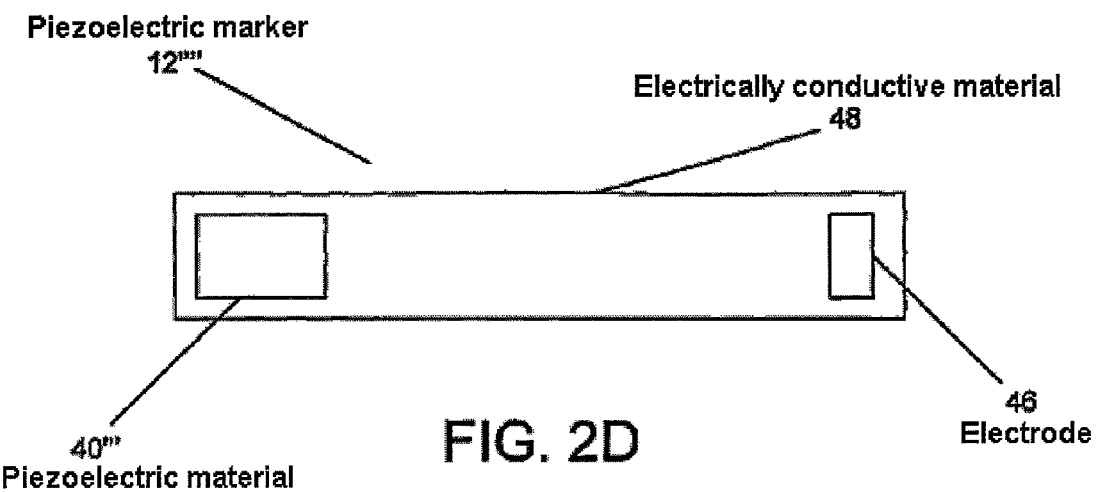

A further embodiment of a piezoelectric marker in accordance with the present invention is illustrated in FIG. 2D. The piezoelectric marker 12'''' includes a piece of piezoelectric material 40''' and an electrode 46 that are embedded in an electrically conductive material 48 that has similar properties to the electrically conductive material 40 used in the construction of the piezoelectric marker 12''' shown in FIG. 2C. In one embodiment, the piece of piezoelectric material has dimensions that are smaller than one half the wavelength of the ultrasound used to excite the piezoelectric marker. The spacing of the piezoelectric material and the electrode using the electrically conductive material can influence the dipole moment of the marker, with generally greater detectable signals from the marker with greater spacing.

Figure 2E:
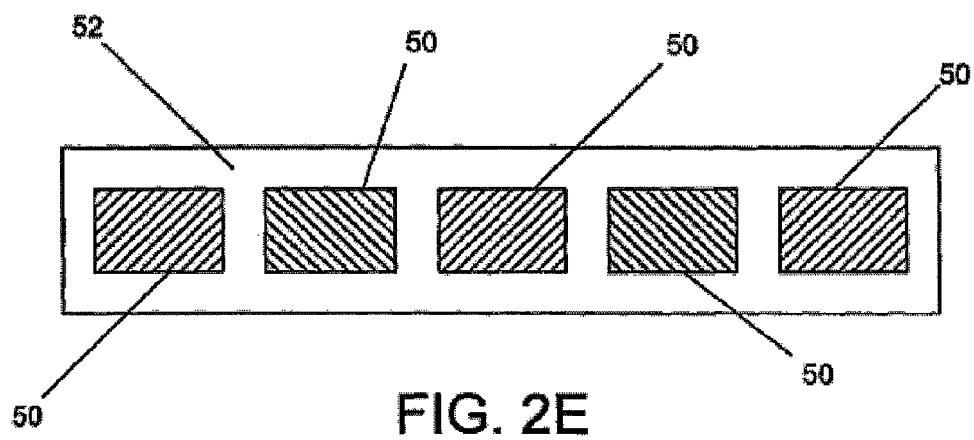

An additional embodiment of a piezoelectric marker in accordance with the present invention that includes multiple pieces of piezoelectric material that are aligned with alternating polarities is illustrated in FIG. 2E. The pieces of piezoelectric material 50 are arranged adjacent each other with alternating polarities such that the pieces of piezoelectric material appear as individual generators sensitive to ultrasound impinging from many directions. The pieces of piezoelectric material are surrounded by a layer of material 52 that is not electrically conductive material.

Figure 2F:
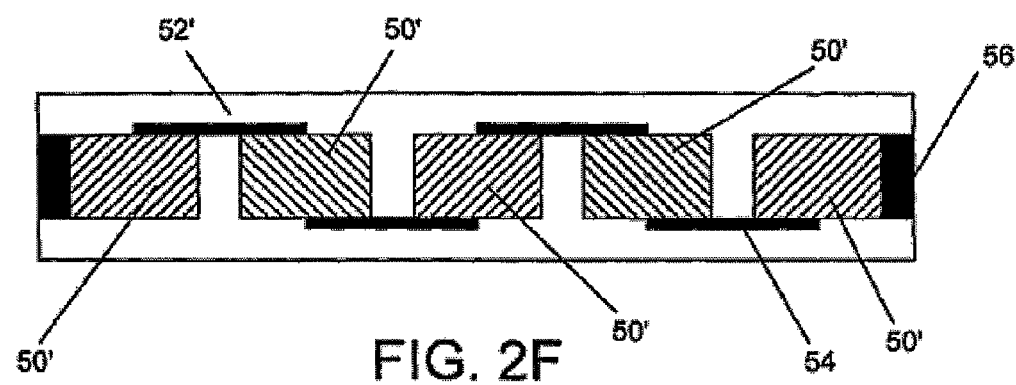

An embodiment of a piezoelectric marker similar to the piezoelectric marker illustrated in FIG. 2E except that the pieces of piezoelectric material are connected in electrical series is shown in FIG. 2F. The pieces of piezoelectric material 50' are connected by strips of electrically conductive material 54 and electrodes 56 are provided adjacent the outermost pieces of piezoelectric material in the array. The array of piezoelectric material and the strips of electrically conductive materials are surrounded by a material 52' similar to the materials shown as 52 in FIG. 2E. The arrangement illustrated in FIG. 2F can enable the pieces of piezoelectric material to produce a larger aggregate signal than would be obtained without electrical connections between the pieces of piezoelectric material.

As mentioned above, any variety of structures can be used to construct piezoelectric markers. The following discussion introduces factors that can impact the electric field generated by a piezoelectric marker in response to incident ultrasound. An appreciation of these factors can, therefore, enable the design of any number of structures that are capable of generating an electric field in response to a given ultrasound signal that is capable of detection at the surface of a subject's body.

In the embodiments of piezoelectric markers described above piezoelectric materials are used to generate electric fields from ultrasound pressure waves. Piezoelectric materials are polarized electrically-attractive materials that generate displacement currents when pressure is applied to their surface. This class of materials includes polymers like polyvinylidene fluoride (PVDF), and ceramics like lead zirconate titanate (PZT). Examples of other piezoelectric materials that could be used include any piezoceramic, polyvinylidene fluoride-trifuoro ethylene (PVDF-TRFE), Lithium Niobate, quartz, Lead Metaniobate, Lead Titanate, Tourmaline or any other material that will generate a potential when excited by a pressure wave such as electron-bombarded plastics.

As already identified above, the dimensions of any pieces of piezoelectric material used in the construction of a piezoelectric marker can influence the electric field generated by the piezoelectric marker. The dimensions of a piezomaterial required for its electrical detection at a given depth is clearly a tradeoff in terms of image resolution and signal to noise ratio. Larger chips create stronger electrical signals and can be seen at greater depth. The ratio of the wavelength of ultrasound incident on the material to the thickness of the piezoelectric material can be particularly important. For example, a thickness equal to half the wavelength of the ultrasound pressure waves would tend to increase the power transfer to the piezoelectric material and increase its voltage output.

An additional factor to consider when dimensioning a piezoelectric material is that the frequency of the evoked electrical responses from piezoelectric markers generally follows the ultrasound acoustic frequency, however, under ultrasound pulse exposure high-Q piezoceramics like PZT will also mechanically ring at their natural resonant frequency in a way that is largely determined by their thickness. Therefore, resonance can be used to increase the magnitude of the electric field generated. In addition, different resonant frequencies can be used to individually identify different piezoelectric markers, marker responding more strongly to a specific ultrasound frequency or producing an electrical frequency characteristic of its natural resonance.

Another important property in selecting a piezoelectric material for incorporation in a piezoelectric marker in accordance with the present invention is the acoustic impedance of the piezoelectric material relative to the tissue in which the marker is embedded. The relative acoustic impedance determines how much of the ultrasound energy is used to generate charge. The remainder of the energy is reflected at the interface between the sound transport medium and the piezoelectric material. In tissue, calculations show that approximately 10% of ultrasound energy is utilized by PZT while about 89% is used by PVDF, because PVDF has an acoustic impedance much closer to that of tissue. As can be seen from the embodiments illustrated in FIGS. 2C, the amount of energy utilized by a piezoelectric material can be increased by coating the piezoelectric material in a layer of material that has an acoustic impedance that more closely matches the acoustic impedance of the tissue. In one embodiment, the layer of material is chosen to have an acoustic impedance in accordance with the formula (where Z is the acoustic impedance):

$$Z_{matcg} = \sqrt{Z_{tissue} Z_{transducer}}$$

In another embodiment, the layer has a thickness of one quarter the wavelength of the ultrasound incident on the piezoelectric marker. Use of a layer having a thickness of one quarter the wavelength of the incident ultrasound can increase the amount of ultrasound energy that is utilized by the piezoelectric material.

Another factor that can influence electrical power transfer is the electrical port impedance of the materials used in the construction of the piezoelectric marker and how they match to the electrical impedance of the tissue at the ultrasound frequency. This characteristic is optimized through selection of the size and composition of the piezoelectric material. In general small chips of piezoelectric materials will be assembled in electrical series to provide an enhanced voltage output in response to an ultrasound wave.

Figure 3A:
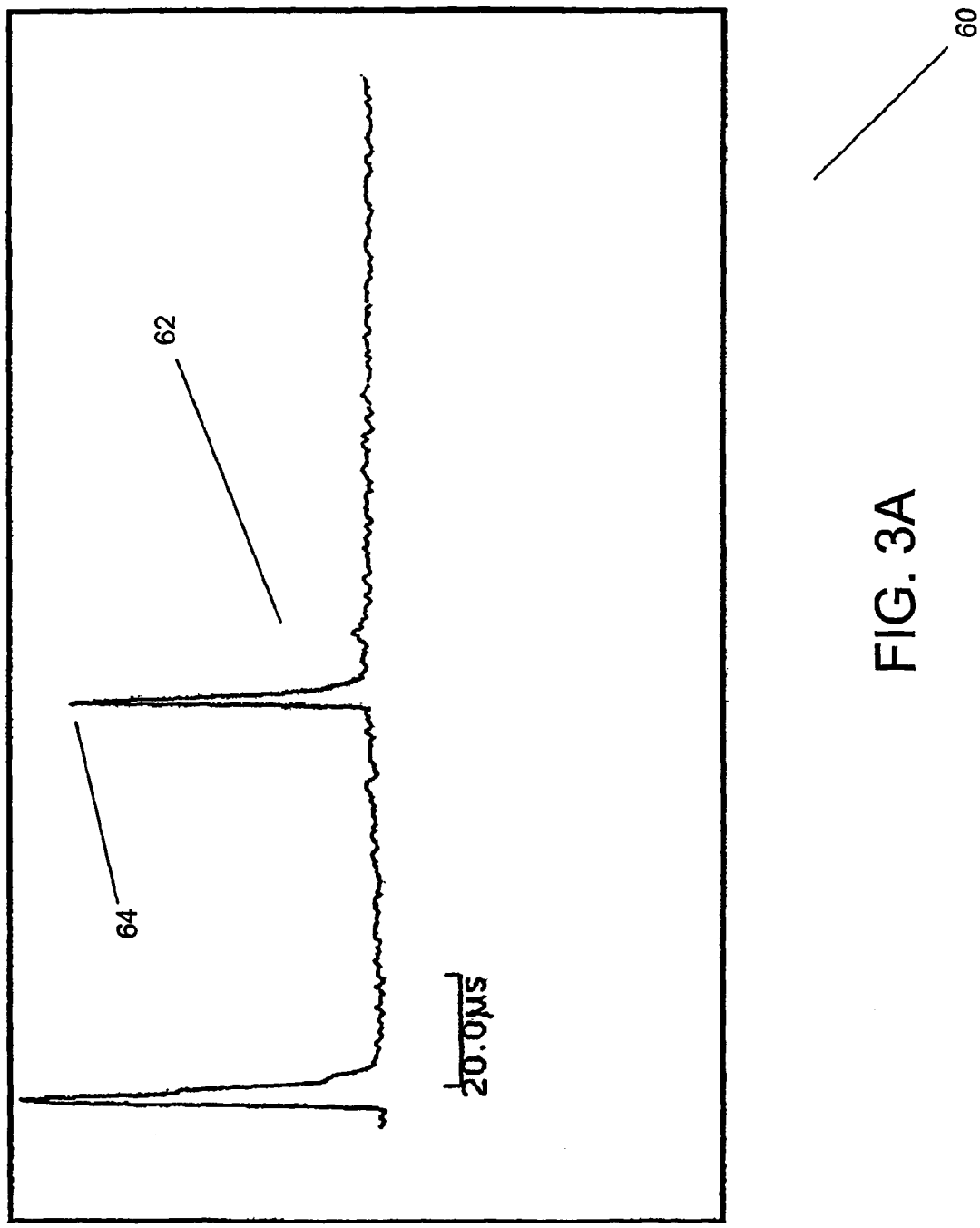
FIGS. 3A and 3B are graphs showing the electric field generated by piezoelectric markers in response to excitation by ultrasound.
Figure 3B:
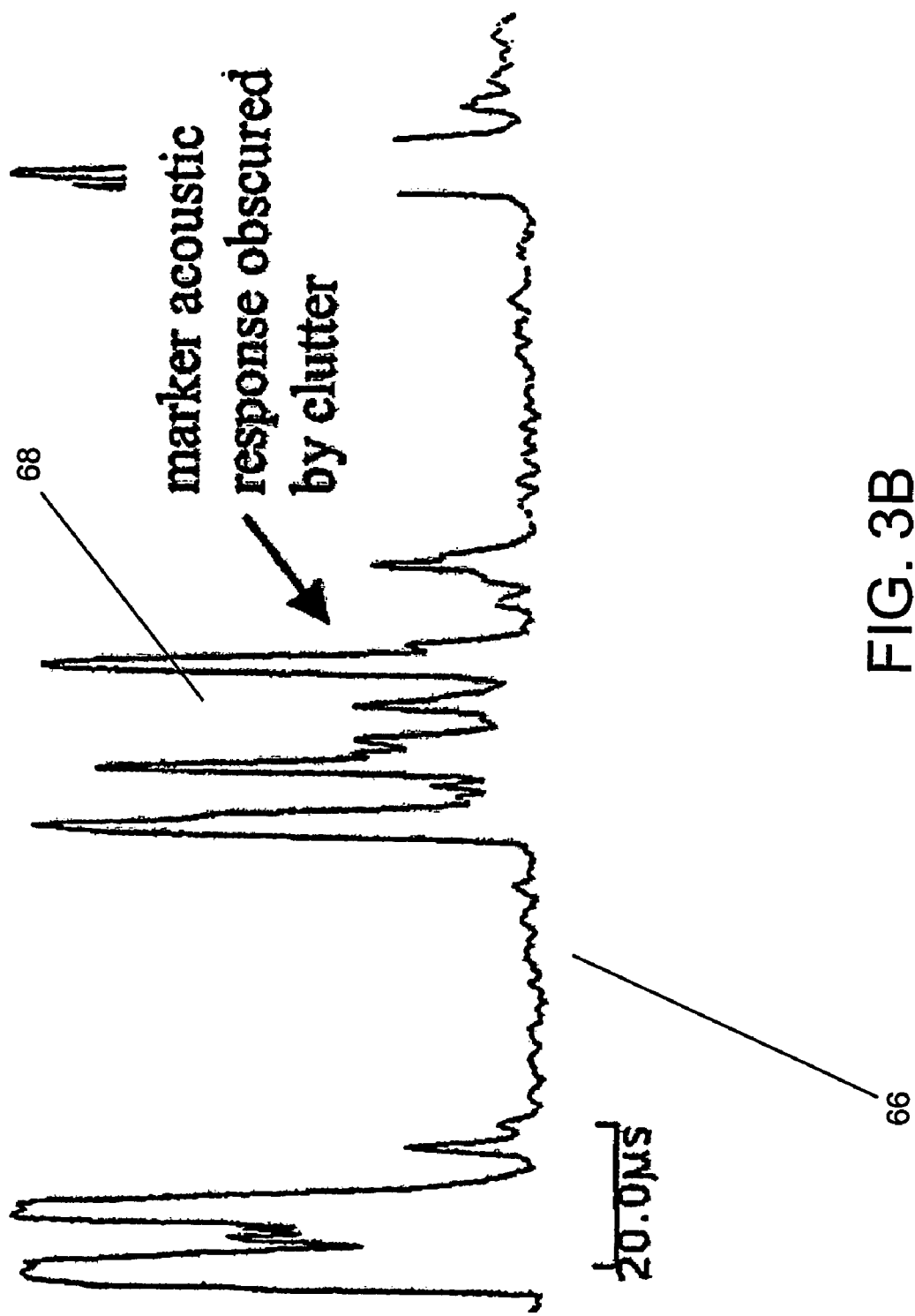

When designing an imaging system in accordance with the present invention, regard should be had to the fact that piezoelectric ceramics and polymers produce about 5-20 mV across their thickness when illuminated by 2.5-7.5 MHz ultrasound at 10 mW/cm2 average energy. If these markers are placed in tissue, several tens to hundreds of microvolts will appear on the skin surface in response to the above ultrasound pressure waves. Ultrasound evoked electrical waveforms from pieces of PVDF and PZT are illustrated in FIGS. 3A and 3B. The graph 60 shown in FIG. 3A includes a plot 62 indicative of an electric field during a period of time in which two ultrasound pulses are incident on a piece of PVDF (one directly from the transducer and the other a reflection from the back surface of the test tank). The graph shows large narrow peaks 64 in the detected electric field. The characteristics of these peaks enable accurate measurements of the distance of the piezoelectric material from the ultrasound transducer. By contrast, the signal 66 shown in FIG. 3B shows the peaks in the plot 68 of the electric field measured when a piece of PZT is excited by similar ultrasound pulses are not nearly as prominent or distinct. Despite the greater magnitude of the electrical response of PVDF, either material may be suitable for use in an embodiment of a piezoelectric marker in accordance with the present invention. Choice of material will largely depend on the magnitude of the electric field that is required to be generated in a particular application and the accuracy required by the application.

Figure 4:
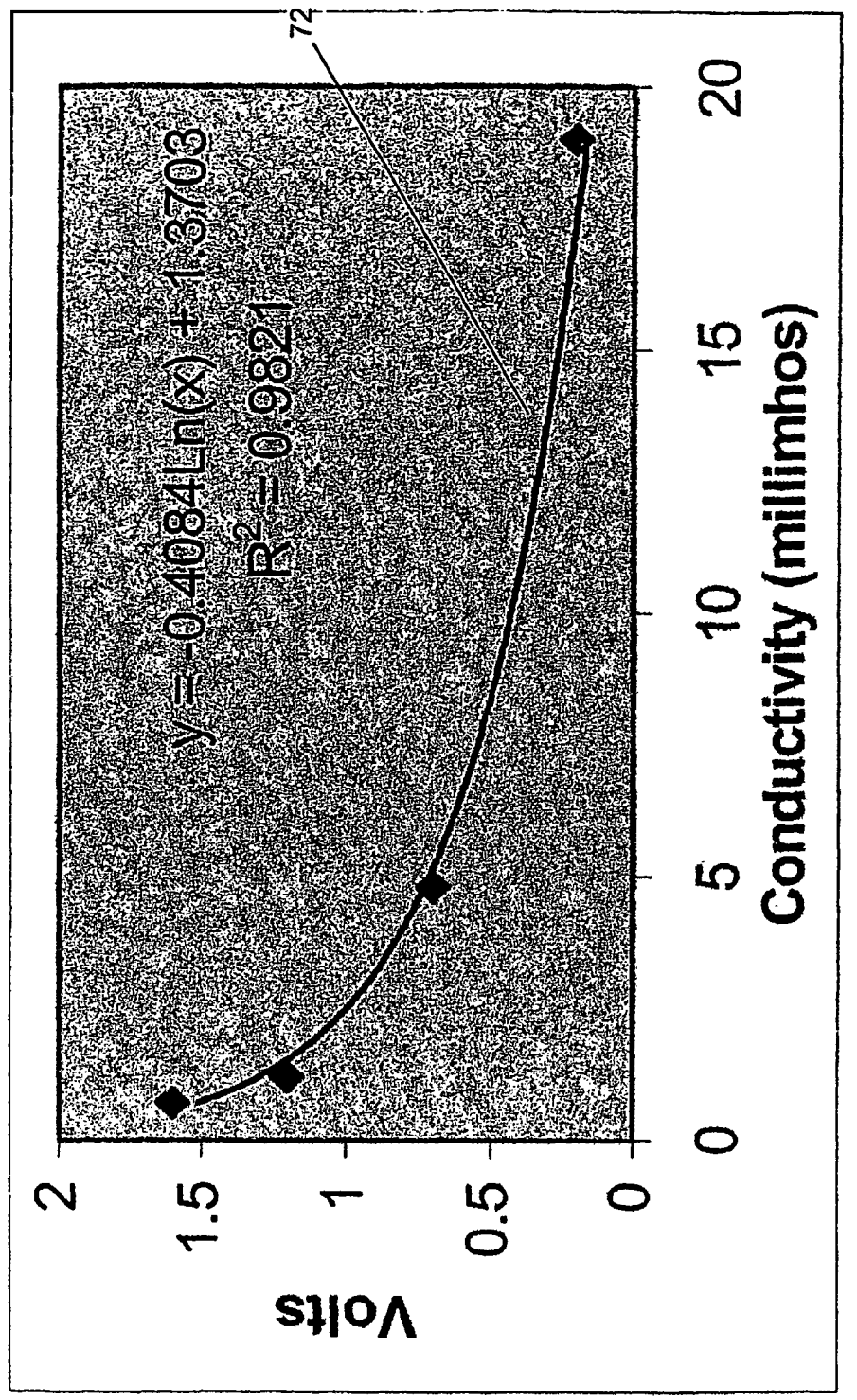
FIG. 4 is a graph showing the magnitude of an electrical waveform generated by a piezoelectric marker that is excited by an ultrasound wave in accordance with one embodiment of the present invention and the variation of this magnitude with the conductivity of the medium surrounding the piezoelectric marker.

A factor that can impact the magnitude of the electric field required to locate a piezoelectric marker in accordance with the present invention is the conductivity of the material in which the marker is surrounded. A graph 70 is shown in FIG. 4 that includes a plot 72 showing the variation on electric field strength with increased conductivity. As conductivity is decreased, the plot shows that the electric field increases asymptotically.

A number of approaches can be taken to constructing an imaging system in accordance with the present invention that is capable of displaying the location of piezoelectric markers. One approach is to construct a custom imaging system in accordance with the schematic diagram shown in FIG. 1. Alternatively, commercial ultrasound diagnostic systems have within them circuitry to sensitively detect, process, and display low-level high frequency electrical signals such as those detected by ultrasound echo-receive transducers. If the detected electrical signals produced by the interaction of sound energy and the piezoelectric material are introduced into the ultrasound signal-processing path, then the imaging system can interpret the signals as acoustic echoes superimposing them on an image generated using actual ultrasound reflections.

Figure 5:
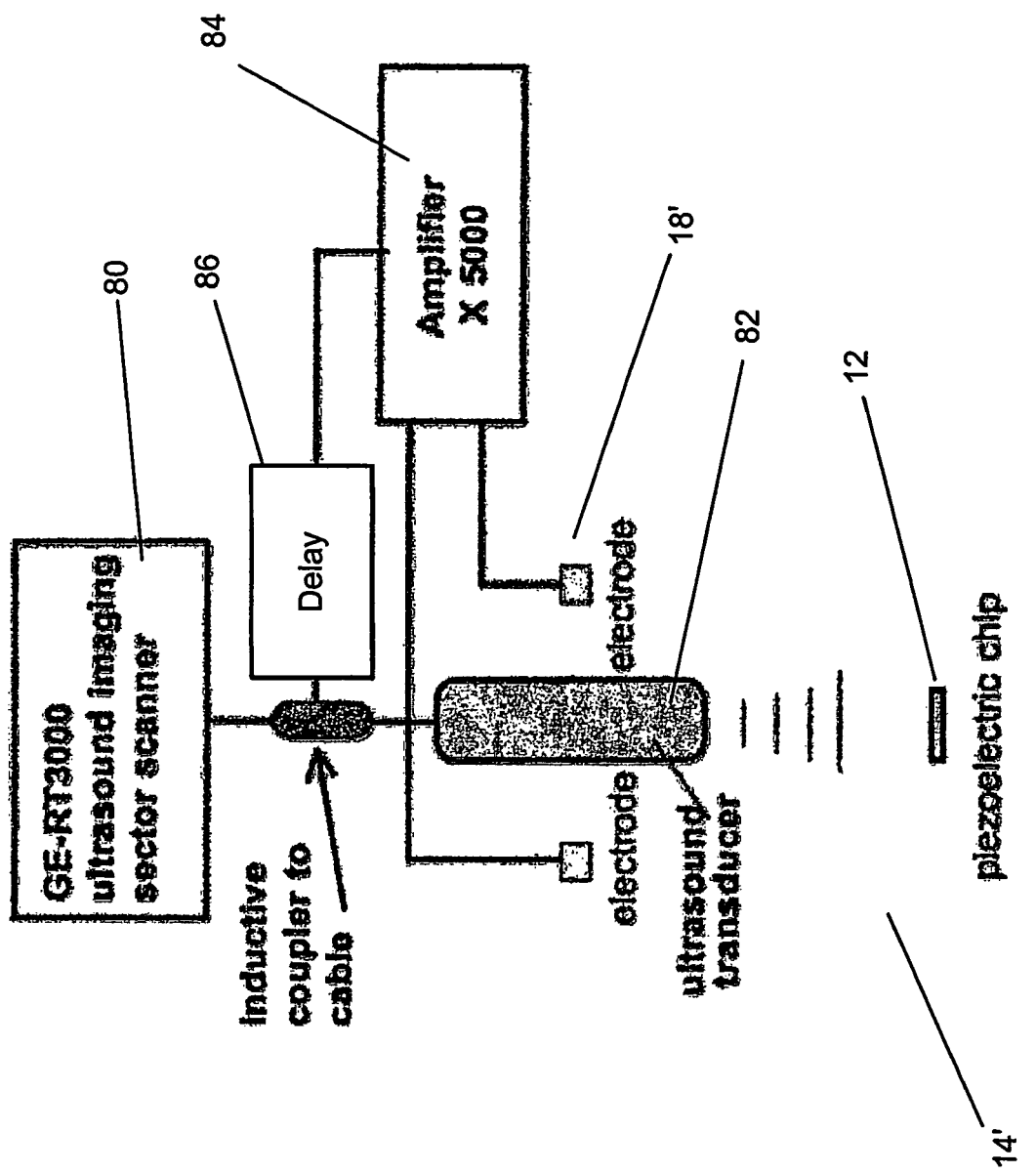
FIG. 5 is a schematic diagram showing an embodiment of an imaging system in accordance with the present invention.

An embodiment of an imaging system in accordance with the present invention that is implemented using a commercial ultrasound diagnostic system is shown in FIG. 5. The imaging system 10' includes a commercial ultrasound diagnostic system 80 that is connected to an ultrasound transducer array 82. The ultrasound transducer 82 is directed toward piezoelectric markers 12 embedded within a subject's body 14'. Electrodes 18' are placed in contact with the subject's body and are connected to an amplifier 84, which is in turn connected to the commercial ultrasound diagnostic machine via a device 86 capable of introducing a delay between the detection of a signal at the electrode and the provision of the signal to the ultrasound diagnostic system.

Due to the fact that ultrasound reflections propogate more slowly than electric fields, a device 86 is required to introduce a delay into the output of the electrodes. Otherwise, the piezoelectric markers would appear in a location that is approximately half the actual distance of the piezoelectric marker to the ultrasound transducer array. The delay can be created by detecting the generation of the acoustic wave by the ultrasound transducer and then sampling the output of the electrodes using a microcontroller with an analog to digital converter. An output can be generated by the microcontroller and the digital to analog converter and coupled into the input of the ultrasound diagnostic system using inductive coupling. The output provided to the ultrasound diagnostic system is the sampled input delayed by an amount sufficient to cause the signal to be provided to the ultrasound diagnostic system at a time after the generation of the ultrasound pulse equal to twice the time between the generation of ultrasound pulse and the time at which the sample of the electrodes was taken. In other embodiments, other components such as discrete components or application specific circuits can be used to achieve delays in either the analog or digital domain.

The delayed output of the electrodes can be provided to a commercial ultrasound diagnostic system, where the electrode signal is treated as if it were an ultrasound reflection. When electrode-detected potentials are added into the signal path of an ultrasound imaging system, the machine can simultaneously form an electrical image of the embedded piezoelectric material along with a conventional acoustic-echo image of the tissue. Contrast for the piezoelectric marker can appear arbitrarily high in the tissue image or displayed in a different color or set to blink as an eye-catching part of the normal diagnostic acoustic image. This is because the electronic signal-processing pathway for the piezoelectric information is mostly separated from that of the acoustic.

In some embodiments, the electrical signal generated by a piezoelectric marker is dependent on the instantaneous position of the ultrasound scanning beam such that the displayed brightness on a similarly scanning beam on a cathode ray tube used in a display in accordance with an embodiment of the present invention is modulated by the detected electrical signal intensity from the medium. The result of this process is a map of the scanned field showing in brightness display regions of evoked electrical response where the ultrasound scanning beam intersects the piezoelectric marker. This process of creating an image shows the electrical image as having characteristics that are substantially different compared to the portion of the image that is generated from ultrasound acoustic echoes.

Another approach that can be used to delay the signal provided to an ultrasound diagnostic system is to apply the piezoelectric signal to a separate input in video display buffer and causing it to time scale the piezoelectric signal to match that of the acoustic signal. One of ordinary skill in the art will appreciate that each commercial ultrasound diagnostic system is likely to require a different approach to achieving the required delay.

In one embodiment, the commercial ultrasound diagnostic system is a 3.5 MHz RT-3000 manufactured by GE Healthcare of Chalfont St. Giles, United Kingdom. In other embodiments, any commercial diagnostic system possessing a first output capable of driving an ultrasound transducer, a first input capable of receiving a signal generated by an ultrasound transducer indicative of reflected ultrasound and a second input capable of receiving a signal having characteristics similar to a signal generated by an ultrasound transducer indicative of reflected ultrasound. In other embodiments, the first output and the first input can be implemented using a single physical connection. In addition, the second input signal can be coupled with the first input signal and the ultrasound diagnostic system need only have a single input capable of receiving signals with characteristics similar to signals generated by an ultrasound transducer in response to reflected ultrasound pressure waves. Examples of other suitable systems include a Picker Echoview-80 ultrasound machine manufactured by Picker International Inc. of Cleveland, Ohio with a 2.25 MHz 8 mm l.f. unit used in A-mode operation. In other embodiments, almost any commercial ultrasound diagnostic system can be adapted to image piezoelectric markers in accordance with practice of the present invention.

In one embodiment, the electrodes can be implemented using silver silver chloride electrodes although in other embodiments other biocompatible electrodes can be used. In one embodiment the pre-amplifiers can be implemented using low noise wide bandwidth amplifiers having a gain of at least×1000 and the delay circuitry can be implemented using digital delay lines.

The ability of imaging systems in accordance with the present invention to locate and display images of piezoelectric markers can be impacted by the configuration of the electrodes used to detect electric fields generated by piezoelectric markers in response to excitation by ultrasound pressure waves. Electrical waves at megahertz frequencies are relatively long in wavelength compared to body dimensions. This means that the marker can be considered as a near field electrical source coupled by a complex impedance to electrodes. The piezoelectric material can be modeled as an oscillating dipolar current source in a volume conductor with the ultrasound impacting a small square chip of piezoelectric material in the direction of its thickness polarization. Induced displacement currents are flowing around the edges of the chip. The electrical field lines from the currents extend into an isotropically conducting medium and ultimately appear at the surface boundary. An electrode placed on the surface measures a potential with respect to another remote electrode.

The amplitude of the potentials detected from imbedded piezoelectric markers can vary as a function of the orientation and distance between the markers and the electrodes. With certain positions of the pickup electrodes relative to the thickness of the piezoelectric marker, the electrodes cannot detect signals generated by the piezoelectric markers. In several embodiments, multiple sets of orthonormal electrodes are placed on the surface of the skin to enable detection of signals generated by the piezoelectric markers. In other embodiments, piezoelectric markers can be used that are polarized in multiple directions.

In several embodiments, the electrodes can be positioned on the subject's body next to the ultrasound transducer scanning-head. In other embodiments, the scanning head and the electrodes are integrated into a single unit. In other embodiments, other locations for the electrodes on the body can be used.

In embodiments where more than two electrodes are utilized, differences in the strength or other characteristics of the signals generated by different electrodes can be interpreted to locate the markers relative to each of the individual electrodes. In several embodiments, electrode positioning and signal processing can be used to locate piezoelectric markers in three dimensions. In one embodiment, three pairs of electrodes are placed on the body surface in pairs frontally, saggitally and coronally in a way similar to the well-known placement called the Frank lead system used for the clinical vectorcardiogram. The electrical signal from these pairs would be combined by electrical analog or digital vector addition as known to those in the art, prior to being introduced into the ultrasound imaging circuitry. The advantage of using multiple pairs of electrodes positioned according is that the resulting piezoelectrical signal can have a constant amplitude regardless of the orientation of the marker within the body.

Figure 6A:
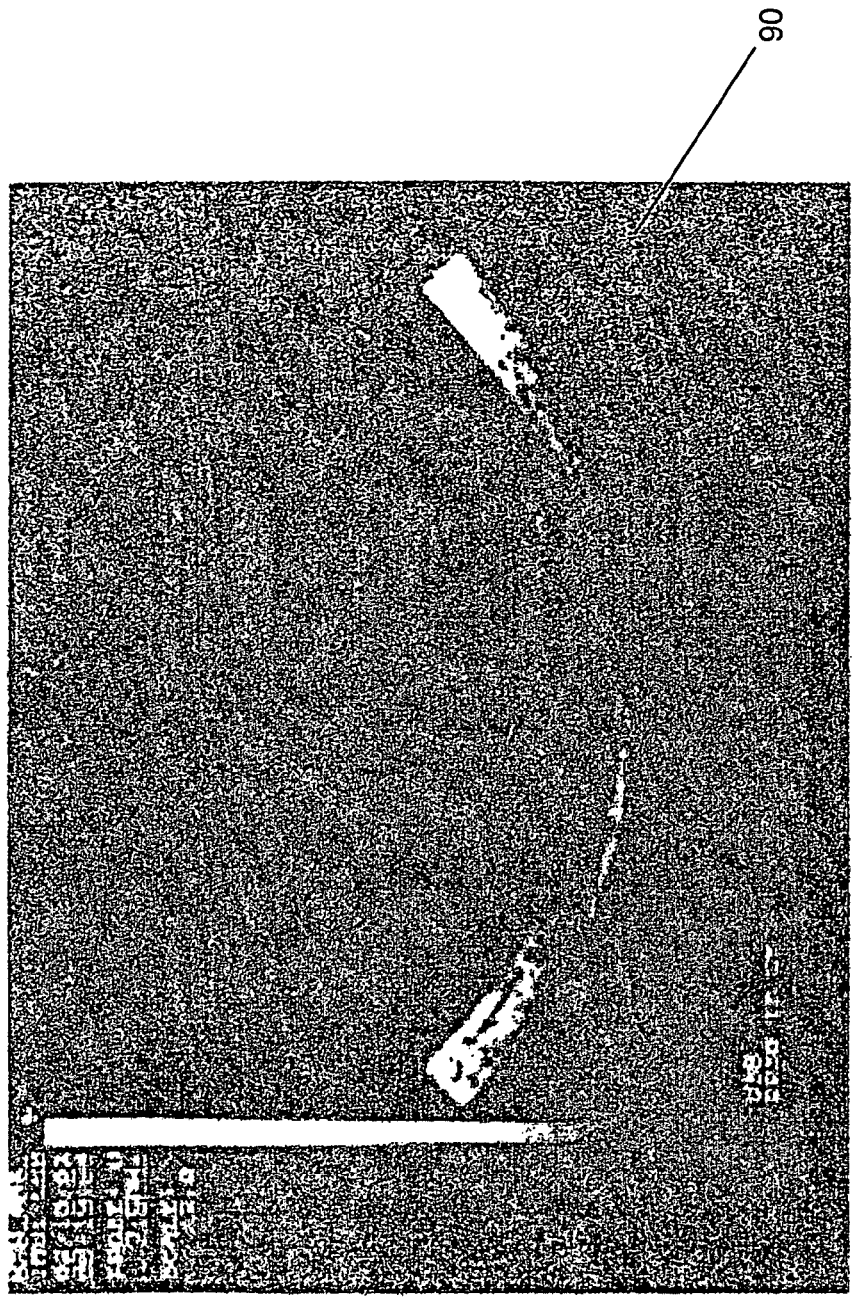
FIG. 6A is a reproduction of the output image of a conventional ultrasound imaging device that is imaging a volume containing a piezoelectric marker in accordance with an embodiment of the present invention.
Figure 6B:
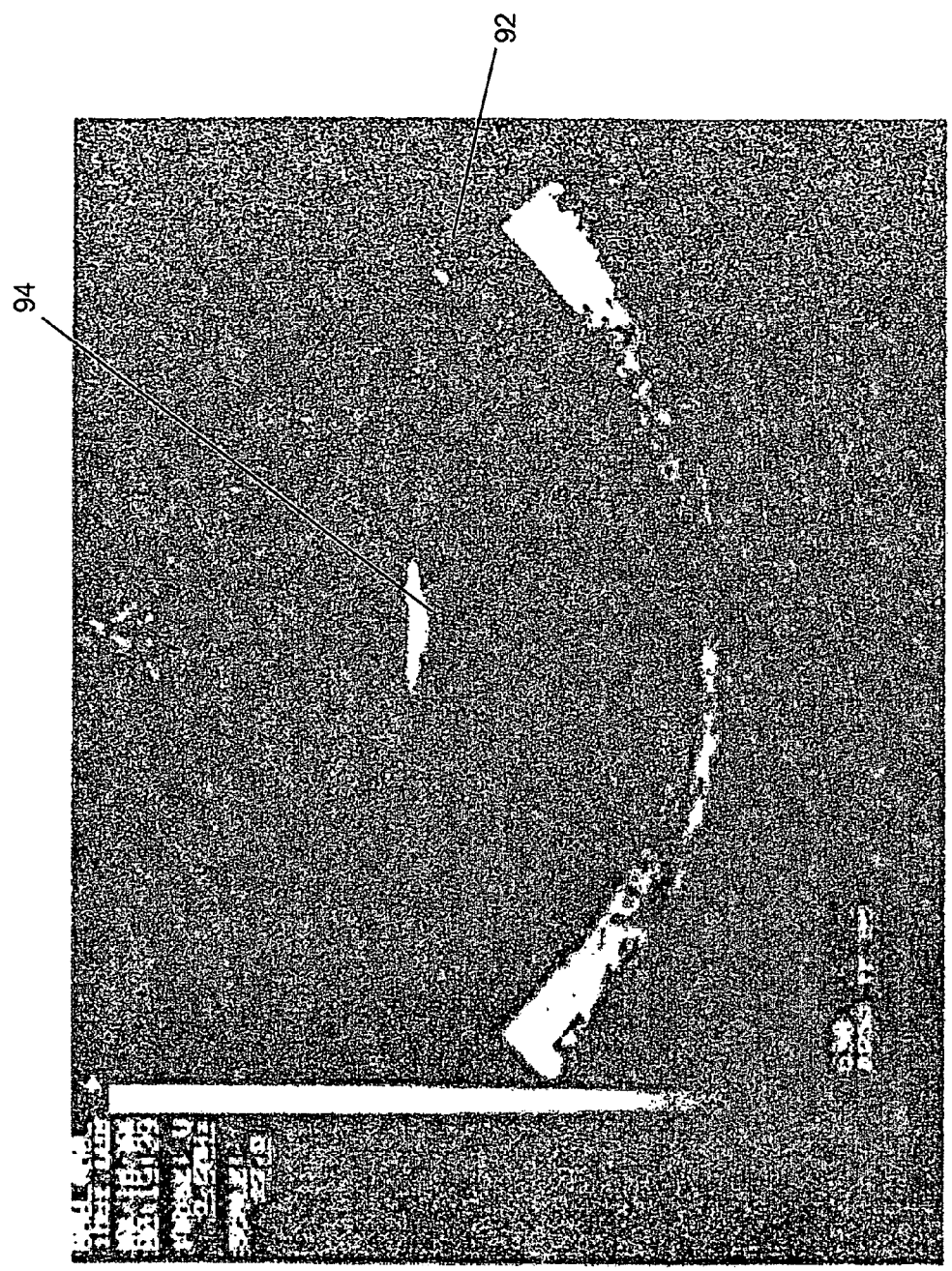
FIG. 6B is a reproduction of the output image generated by an imaging system in accordance with the present invention that is imaging a volume containing a piezoelectric marker in accordance with an embodiment of the present invention.

A display 90 generated by a commercial ultrasound diagnostic system when ultrasound pulses are directed towards a piezoelectric marker in accordance with the present invention is shown in FIG. 6A. This display can be compared with the display 92 shown in FIG. 6B that was generated in accordance with the present invention by combining information from electrodes with information from the ultrasound transducer. The conventional display 90 does not show the piezoelectric marker 94 as clearly as the display generated in accordance with the present invention.

In one embodiment, piezoelectric markers can be used as positional aides for body alignment during medical procedures. In other embodiments, piezoelectric markers can be included in medical devices to assist in locating or positioning medical devices within the body. Such markers can be used as fiducial markers that show up under ultrasound imaging for stereotactic positioning the head and other parts of the body in MR, CT and PET imaging systems. Markers can also be attached to various and multiple parts of body organs such as the heart to allow visualization of the cardiac motion of the chambers and to assess cardiac performance.

In other embodiments, the markers can provide enhanced operation of the ultrasound diagnostic modes known as M-mode and Doppler modes. In m-mode, the electrical signals from a moving piezoelectriccal marker, attached to the heart, for example, will clearly identify it in the conventional M-mode operating mode in a way essentially the same as in conventional M-mode imaging except that the marker's location will appear bright and in high contrast.

Likewise, switching an ultrasound imaging system modified in accordance with the present invention to Doppler mode can cause the marker to appear and its velocity of motion to appear on the display as a marker. This provides a convenient method for identifying and labeling the piezoelectric markers specific structures that are in motion. In this operating modality, the apparent Doppler shifted frequency will be one half of the comparable values from that of moving tissue acoustic echoes and so, as in the case of imaging, the Doppler shift in the electrical channel will be doubled to be comparable to the Doppler shift of ultrasound reflections caused by moving tissue.

Figure 7:
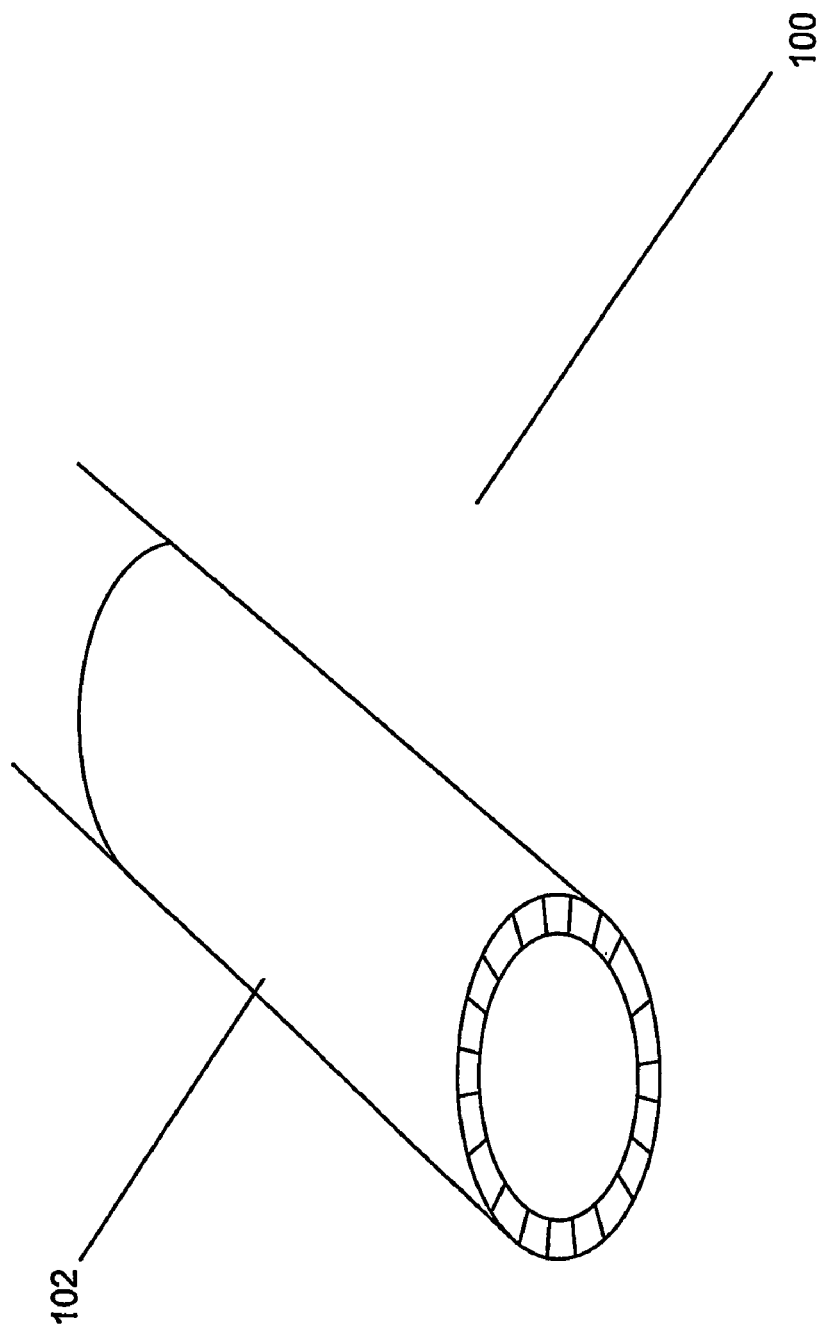
FIG. 7 is a schematic view of a medical device including a piezoelectric marker in accordance with one embodiment of the present invention.

An embodiment of a biopsy needle in accordance with the present invention is illustrated in FIG. 7. The biopsy needle 100 is constructed so that a portion of the needle acts as a piezoelectric marker 102. In one embodiment, the piezoelectric marker is constructed from PVDF that is polarized radially as it is extruded to enable detection from numerous orientations of the electrodes relative to the position of the biopsy needle.

While the above description contains many specific embodiments of the invention, these should not be construed as limitations on the scope of the invention, but rather as an example of one embodiment thereof Many other variations are possible. Accordingly, the scope of the invention should be determined not by the embodiments illustrated, but by the appended claims and their equivalents.

What is claimed is:

1. An imaging system comprising:
a piezoelectric marker embedded in a subject's body, wherein the piezoelectric marker comprises at least one piece of piezoelectric material;
an ultrasound transducer connected to an ultrasound pulser and a receiver, where the ultrasound transducer is configured to excite the piezoelectric marker;
a computer sequencing control connected to the receiver and the ultrasound pulser;
a display connected to the computer sequencing control; and
electrodes residing outside the subject's body and connected to the computer sequencing control via amplification circuitry.

2. The imaging system of claim 1, wherein the piezoelectric marker comprises PVDF.

3. The imaging system of claim 1, wherein the piezoelectric marker comprises PZT.

4. The imaging system of claim 1, wherein the piezoelectric marker comprises PVDF-TRFE.

5. The imaging system of claim 1, wherein the piezoelectric marker comprises multiple pieces of piezoelectric material arranged such that adjacent pieces have alternating polarities.

6. The imaging system of claim 1, wherein the piezoelectric material in the piezoelectric marker is coated with a layer of material having an acoustic impedance that is less than the acoustic impedance of the piezoelectric marker.

7. The imaging system of claim 1, wherein the computer sequencing control, the ultrasound pulser, the receiver and the display are implemented using an ultrasound diagnostic machine.

8. A method of imaging an object embedded in a subject's body, comprising:
exciting the object with ultrasound;
generating electric fields through the use of a piezoelectric marker; and
forming an image using information collected from reflected ultrasound and information collected concerning electric fields by electrodes outside a subject's body.

9. The method of claim 8, wherein the information collected concerning electric fields is delayed relative to the information collected from the reflected ultrasound.

10. The method of claim 9, wherein:
the object is excited using pulses of ultrasound; and
the delay is equal to twice the time between the generation of the most recent ultrasound pulse and the time at which the electric field is observed.

11. An imaging system comprising:
a piezoelectric marker adapted to be embedded inside a subject's body and configured to generate an electric field in response to an ultrasound pulse; and
a plurality of electrodes outside the subject's body, wherein said electrodes are configured to detect said electric field.

12. The imaging system of claim 11, wherein the piezoelectric marker comprises PVDF.

13. The imaging system of claim 11, wherein the piezoelectric marker comprises PZT.

14. The imaging system of claim 11, wherein the piezoelectric marker comprises PVDF-TRFE.

15. The imaging system of claim 11, wherein the piezoelectric marker comprises multiple pieces of piezoelectric material arranged such that adjacent pieces have alternating polarities.

16. The imaging system of claim 11, wherein the piezoelectric material in the piezoelectric marker is coated with a layer of material having an acoustic impedance that is less than the acoustic impedance of the piezoelectric marker.

17. The imaging system of claim 11, wherein the computer sequencing control, the ultrasound pulser, the receiver and the display are implemented using an-ultrasound diagnostic machine.

* * * * *

UNITED STATES PATENT AND TRADEMARK OFFICE
CERTIFICATE OF CORRECTION

| | |
|---|---|
| PATENT NO. | : 8,282,561 B2 |
| APPLICATION NO. | : 10/557362 |
| DATED | : October 9, 2012 |
| INVENTOR(S) | : Bruce Towe |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1566 days.

Signed and Sealed this
Tenth Day of June, 2014

Michelle K. Lee
*Deputy Director of the United States Patent and Trademark Office*